United States Patent [19]

Patel et al.

[11] Patent Number: 4,935,350

[45] Date of Patent: Jun. 19, 1990

[54] MATERIALS AND METHODS FOR CONTROLLING PLASMID COPY NUMBER AND STABILITY

[75] Inventors: Avantika C. Patel; Barry J. Ratzkin, both of Thousand Oaks, Calif.

[73] Assignee: Amgen, Thousand Oaks, Calif.

[21] Appl. No.: 798,825

[22] Filed: Nov. 18, 1985

[51] Int. Cl.$^5$ .................... C12N 15/00; C12P 21/00; C12P 21/02

[52] U.S. Cl. ................... 435/69.4; 435/69.1; 435/172.3; 435/257; 935/13; 935/28; 935/37; 935/56; 935/69

[58] Field of Search .............. 435/68, 91, 172.3, 255, 435/256, 320; 935/13, 28, 37, 28, 37, 56, 69

[56] References Cited

U.S. PATENT DOCUMENTS

| | | | |
|---|---|---|---|
| 4,464,472 | 1/1989 | Carbon et al. ............... | 435/68 |
| 4,511,652 | 4/1985 | Lin ............................ | 435/29 |
| 4,703,008 | 10/1987 | Fogel et al. ................. | 435/240.2 |

FOREIGN PATENT DOCUMENTS

| | | | |
|---|---|---|---|
| 123294 | 3/1983 | European Pat. Off. ........... | 435/60 |
| 134773 | 3/1989 | European Pat. Off. ........... | 435/68 |
| 96491 | 4/1989 | European Pat. Off. ........... | 435/68 |
| WO8304053 | 1/1983 | PCT Int'l Appl. ............... | 435/68 |
| WO8401172 | 1/1989 | PCT Int'l Appl. ............... | 435/68 |
| WO8502610 | 2/1989 | PCT Int'l Appl. ............... | 435/68 |
| 1557774 | 1/1989 | United Kingdom .............. | 435/68 |

OTHER PUBLICATIONS

Hill et al. *J. Cell Biochem.*, Supp. 9C p. 137 (1985).
Tschumper et al. Gene, vol. 23, pp. 221–232, 1983 "Copy Number Control by a Centromere".
Panzeri et al. *Chromosomes Today* vol. 8, pp. 46–58, 1984 (Cited page 9 of specification).
Jiminez et al. Nature, vol. 287, pp. 869–871, 1980, "Expression of Transposable Antibiotic Resistance in *Sacaharomyceo*".
Chlebowicz et al., Gene, vol. 39, 1985, pp. 25–31, "Construction of multicopy yeast plasmids with regulated centromere function".
Beggs, Nature, 275, 104–109 (1979).
Bitter et al., Gene, 32, 263–274 (1984).
Bloom et al., Cell, 29, 305–317 (1982).
Bloom et al., J. Cell. Biol., 99, 1559–1568 (1984).
Burnette, Anal. Biochem., 112, 195–203 (1981).
Butt et al., Proc. Nat'l Acad. Sci. (U.S.A.), 81, 3332–3336 (1984).
Clarke et al., Nature, 287, 504–509 (1980).
Dorfman, Genetic Engineering News, May/June, 8 (1983).
Erhart, J. Bacteriol., 156, 625–635 (1983).
Fitzgerald-Hayes et al., Cell, 29, 235–244 (1982).
Hanahan, J. Mol. Biol., 166, 559–580 (1983).
Hill et al., J. Cell. Biochem., Supp. 9C, 134 (1985).
Hohmann et al., Virology, 125, 432–444 (1983).
Johnston et al., Mol. Cell. Biol., 4, 1440–1448 (1984).

(List continued on next page.)

Primary Examiner—Robin L. Teskin
Attorney, Agent, or Firm—Marshall, O'Toole, Gerstein, Murray & Bicknell

[57] ABSTRACT

Methods and constructions for controlling the copy number and for maintaining the stability of a plasmid in yeast cells involving inserting into the plasmid a centromere sequence under the transcriptional control of a regulatable promotor. The promoter is not activated when it is desirable to maintain a copy number of one per haploid cell (e.g. during a culture growth phase) but is activated when expression is desired. When the promoter is inactive, the centromere sequence causes the plasmid to behave as a minichromosome, but upon activation of the promoter transcription through the centromere sequence permits an increase in copy number. Multicopy plasmids are selected for by inserting a G418 resistance gene in the plasmid. Medium concentrations of greater than about 400 μg/ml of G418 will select for cells containing multiple copies of the plasmid while lesser concentrations of G418 select for cells containing a single copy of a plasmid containing G418$^R$ gene and against cells containing no copy of the G418$^R$ gene.

21 Claims, 4 Drawing Sheets

OTHER PUBLICATIONS

Karin et al., Proc. Nat'l Acad. Sci. (U.S.A.), 81, 337–341 (1984).
Kuo et al., Mol. Cell. Biol., 3, 1730–1777 (1983).
Meacock et al., Cell, 20, 529–542 (1980).
Miyajima et al., Mol. Cell. Biol., 4, 407–414 (1984).
Remaut et al. Gene, 22, 103–113 (1983).
Rigby et al., J. Mol. Biol., 113, 237 (1977).
Southern, J. Mol. Biol., 98, 503–517 (1975).
Srienc et al., Mol. Cell. Biol., 5, 1676–1684 (1985).
Stinchcomb et al., Nature 282, 39–43 (1979).
Stinchcomb et al., Proc. Nat'l Acad. Sci. (U.S.A.), 77, 4559–4563 (1980).
Struhl et al., Proc. Nat'l Acad. Sci. (U.S.A.), 76, 1035–1039 (1979).
Thomas, Proc. Nat'l Acad. Sci. (U.S.A.), 77, 5201–5205 (1981).
Tschumper et al., Gene, 10, 157–166 (1980).
Uhlin et al., Gene, 6, 91–106 (1979).
Yanisch-Perron et al., Gene, 33, 105–119 (1982).
Zoller et al., Methods in Enzymology, 100, 468–500 (1983).

MATERIALS AND METHODS FOR CONTROLLING PLASMID COPY NUMBER AND STABILITY

BACKGROUND

The present invention relates in general to methods for controlling plasmid copy number and to plasmids constructed according to such methods. In particular, the present invention relates to methods and centromere-containing plasmids for the production of human erythropoeitin in yeast.

Microorganisms, including bacteria and yeasts, have been transformed by exposure to foreign genetic material in order to cause them to express exogenous genes (i.e. genes which do not naturally occur in the organism transformed). There is particular interest in the expression of mammalian gene products in yeast cells. Unlike bacteria, yeast cells share with mammalian cells the ability to glycosylate (i.e. to attach carbohydrates to) proteinaceous gene products. Furthermore, an extensive technology for the fermentation of yeast has been developed in the baking and brewing industries and yeasts appear on the list of organisms generally recognized as safe.

An exogenous gene may be prepared for introduction into a yeast cell by incorporating the gene into a vector. One type of vector is a circular, double-stranded DNA structure, called a plasmid, which replicates independently of the chromosomal DNA that forms the bulk of the hereditary material in the cell. Plasmids may be introduced into yeast cells by a process known as transformation.

A yeast-bacterial shuttle vector is a type of plasmid which contains a DNA replication initiation site, such as the chromosomal arsl sequence or the so-called $2\mu$ origin of replication, which is recognized by the replication enzymes and factors of yeast cells. Yeast-bacterial shuttle vectors also contain an origin of replication from a bacterial plasmid which includes including an initiation site recognized by the replication enzymes and factors of bacterial cells. Beggs, Nature, 275, 104-109 (1979); Stinchcomb, et al., Proc. Natl. Acad. Sci. (USA), 77, 4559-4563 (1980).

Yeast-bacterial shuttle vectors are able to replicate in and may be selected in and recovered from bacteria, such as Escherichia coli (E. coli). It is generally convenient to construct and to amplify (i.e. multiply) plasmids in bacteria.

Yeast-bacterial shuttle vectors are also able to replicate in and may be selected in and recovered from yeasts, such as Saccharomyces cerevisiae (S. cerevisiae). In yeasts these plasmids may be used as transformation vectors for obtaining the expression of foreign DNA.

Yeast-bacterial shuttle vectors may contain a marker which permits selection of cells transformed by the vector. For example, a shuttle vector designated YRP7 contains the trpl gene, which codes for an enzyme called N-(5'-phosphoribosyl) anthranilate isomerase that is necessary for the production of the essential amino acid tryptophan. The trpl gene may be used as a marker by culturing cells in a tryptophan-deficient medium wherein only those cells having the trpl gene survive. Struhl, et al., Proc. Natl. Acad. Sci. (USA), 76, 1035-1039 (1979).

Despite their utility as vehicles for the expression of exogenous genes, yeast-bacterial shuttle vectors are more unstable than are recombinant plasmids in bacteria. For example, autonomously replicating plasmids containing an ars replicator are extremely unstable during cell division and are quickly lost under nonselective culture conditions. Stinchcomb, et al., Nature, 282, 39-43 (1979). One significant aspect of plasmid instability is that cultures of yeast may not be grown for many generations in a fermenter without extensive loss of the vector.

In bacteria, the maintenance of recombinant plasmids in host cells during host cell growth and the expression of heterologous genes incorporated in those plasmids may be facilitated by contol over two functions. Control over a partitioning function (i.e., the function which controls the distribution of plasmids among daughter cells during cell division) assures plasmid stability by preventing random loss of plasmids. Control over a replication function allows enhancement of heterologous gene expression by the amplification of plasmid copy number at a time close to cell harvest when the expression of toxic heterologous gene products does not interfere with host cell growth. Molin, et al., PCT Publication No. WO 84/01171.

Stable maintenance of plasmids in dividing cells requires that each daughter cell receive at least one copy of the plasmid. Thus, in the absence of a mechanism for accurately partitioning plasmids, plasmids are distributed on a purely random basis. One consequence of a random distribution of plasmids is that some daughter cells do not recieve a copy. Although a partition-defective plasmid may be maintained in a cell population by selecting for a marker (e.g., resistance to an antibiotic) associated with the plasmid, continuous application of selection pressure is difficult and expensive.

For example, selective markers useful in S. cerevisiae include a plasmid-borne, drug-resistant, type II dihydrofolate reductase gene (R-dhfr) [Miyajima, et al., Mol. Cell. Biol., 4, 407-414 (1984)] and the leu2-d, an allele of the Leu2 gene [Erhart, J. Bacteriol., 156, 625-635 (1983)]. Selection pressure on the R-dfhr markers is applied by growing cells in a medium including methotrexate. Plasmids having the leu2-d allele may be selected for by growth in leucine-deficient medium. Thus, cells containing at least one but an unknown number of marker plasmids may be selected. However, it is believed that for either of these markers, plasmid copy number is not known to provide a means for selecting for cells containing multiple copies of a plasmid and for selecting against cells containing a single copy of the plasmid.

In another approach to control of the partitioning function, incorporation of the par locus in a bacterial plasmid stabilizes an otherwise unstable plasmid by providing proper partitioning among daughter cells. Meacock, et al, Cell, 20, 529-542 (1980); Molin, et al., PCT Publication No. WO 84/01172.

Bacterial plasmid vectors are also available which provide for thermoinducible expression and temperature-regulated amplification of copy number. Uhlin, et al., U.K. Patent Application No. 1,557,774; Uhlin, et al., Gene, 6, 91-106 (1979); Remaut, et al., Gene, 22, 103-113 (1983). However, control of plasmid copy number, of the sort found in so-called "runaway" plasmids which amplify when released from some form of thermal inhibition on replication, is not available in yeasts. Dorfman, Genetic Engineering News, May/June, 8 (1983). Furthermore, even in bacteria, the large size of these runaway plasmids and their high basal copy number may divert the energy of the host cell from replication of DNA or mRNA to replication of the plasmid nucleic acid. A high basal copy number also increases the potential for poisoning of the host cell by toxic recombinant gene products. Thus, there is a need for some mechanism to balance the need for high copy number at expression and a low copy number during growth.

Centromere DNA sequences (CEN), isolated from chromosomes of *S. cerevisiae*, may be introduced into autonomously replicating yeast plasmids in order to stably maintain the plasmids through mitosis and meiosis. Bloom et al., *Cell*, 29, 305–317 (1982). Any one of five CENs, CEN3, CEN4, CEN5, CEN6 and CEN11, confers stability upon a plasmid into which it is introduced. Bloom, et al., *J. Cell. Biol.*, 99, 1559–1568 (1984). CEN-containing plasmids are stably maintained through mitosis in the absence of selective pressure and segregate in the manner expected for centromere-linked genes. Plasmids containing a functional centromere are kept to a low copy number of 1 to 2 copies per cell. Clarke, et al., *Nature*, 287, 504–509 (1980). A block on replication at the CEN locus may prevent the completion of plasmid replication until anaphase. Tschumper et al., *Gene*, 23, 221–232 (1983). Such plasmids, containing a replication site and a centromere, are also called minichromosomes. Carbon, et al., U.S. Pat. No. 4,464,472.

The copy number control system of the endogenous $2\mu$ plasmid of yeast provides for multiple rounds of plasmid replication when plasmid copy number is low. Plasmid copy number is thereby maintained at about 50 to 100 copies per cell. Beggs, *Nature*, 275, 104–109 (1978). Thus, although the $2\mu$ system (which includes a replication sequence) prevents random loss of plasmids, it does not control plasmid segregation. Tschumper, et al., supra.

In plasmids containing both the CEN and $2\mu$ copy number control mechanisms, the CEN mechanism dominates to result in normally segregating, composite plasmids of a copy number of 1 to 2 per cell. Tschumper, et al., supra. A CEN sequence may be inserted into a plasmid under the replication control of an ars in order to stabilize a CEN-containing plasmid. Srienc, et al., *Mol. Cell. Biol*, 5, 1676–1684 (1985).

In a different type of approach to coupling gene amplification with plasmid stability, a foreign gene is inserted into the downstream flanking region of the yeast copper chelatin gene on a minichromosome (i.e., a plasmid containing a yeast a CEN sequence) including an ars sequence. The locus containing the copper chelatin gene, the CUP1 locus, controls copper resistance in *S. cerevisiae*. The copper chelatin gene is present at a copy number which varies from one per cell in copper-sensitive strains, to as many as 10 or more tandemly iterated copies per cell in copper-resistant strains. Karin, et al., *Proc. Natl. Acad. Sci.* (USA), 81, 337–341 (1984). In the absence of copper, the copy number of a copper chelatin gene remains at an initial level, but when stressed by the introduction of copper, the copper chelatin gene and any exogenous gene inserted into its downstream flanking sequence form tandem multiple repeats in a minichromosome into which they are introduced. Fogel, et al., European Patent Application No. 96,491. However, this approach does not provide means for permitting the amplification of plasmid copy number.

SUMMARY OF THE INVENTION

A vector according to the present invention for the expression of a foreign gene in a microorganism includes an autonomous replication sequence. The vector also includes a promoter, and a terminator defining a region of termination for transcription initiated at the first promoter. A centromere sequence is located between the promoter and the terminator.

Another vector according to the present invention for the expression of an erythropoietic foreign gene in a microorganism includes: an autonomous replication sequence. The vector also includes a first promoter; a first terminator defining a region of termination for transcription initiated at the first promoter; and a centromere sequence between the first promoter and the first terminator. The vector also comprises a second promoter, a second terminator defining a region of termination for transcription initiated at the second promoter, and a gene encoding an erythropoeitic polypeptide between the second promoter and the second terminator.

A method according to the present invention provides reversible control of vector copy number and maintains vector stability. A first promoter is inserted into a vector along with a terminator defining a region of termination for transcription initiated at the promoter, and along with a centromere sequence between the promoter and the terminator.

Another method according to the present invention provides reversible control of plasmid copy number, cell lines having multiple copies of centromere-containing plasmids and maintains plasmid stability. The method involves inserting into the plasmid a promoter, a terminator defining a region of termination for transcription initiated at the promoter, and a centromere sequence between the promoter and the terminator.

Yet another method according to the present invention provides reversible control of vector copy number and maintains vector stability. A copper chelatin promoter is inserted into a vector along with a copper chelatin terminator defining a region of termination for transcription initiated at the copper chelatin promoter, and a centromere sequence between said copper chelatin promoter and said copper chelatin terminator.

Still another method according to the present invention provides for selecting cells containing multiple copies of a plasmid including a gene encoding G418 resistance. Cells are cultured in a medium preferably comprising greater than about 400 $\mu$g/ml of G418.

A further method according to the present invention provides reversible control of vector copy number and maintains vector stability. The method involves inserting into a vector a copper chelatin promoter, a copper chelatin terminator defining a region of termination for transcription initiated at the copper chelatin promoter, and a centromere sequence between the copper chelatin promoter and the copper chelatin terminator. A cell is transformed with the vector and the cell is cultured in a medium having a lower copper concentration than the concentration required to activate transcription at the copper chelatin promoter. The conditions of culture are then altered so that the medium has at least the copper concentration required to activate transcription at the copper chelatin promoter after which the cell is cultured in a medium preferably comprising G418.

Another aspect of the present invention involves a stable strain of cells including cells having multiple copies of a centromere-containing plasmid.

DETAILED DESCRIPTION

CEN functions may be disturbed with transcribing RNA polymerase molecules. Panzeri, et al., *Chromosomes Today,* 8, 46-58 (1984). An inducible centromere may be constructed by placing CEN3 sequences adjacent to the yeast GAL1 promoter. Growth on galactose induces transcription from the promoter and inactivates CEN function, growth on glucose represses transcription and the CEN3 sequences behave as stabilizing elements. Hill, et al., *J. Cell. Biochem., Supp.* 9C, 134 (1985). However, it is believed that prior to the present invention, transcriptional control of centromere function had not been applied to the control of plasmid copy number. Furthermore, prior to the present invention, it was not believed possible to produce a strain of cells having multiple copies of a centromere-containing plasmid stably retained within a cell of the strain.

According to the present invention, a plasmid may be stabilized by the insertion of a centromere DNA sequence which blocks the completion of plasmid replication until anaphase and which assures proper segregation of the plasmid as a minichromosome. The present invention also involves placing the inserted centromere sequence under the transcriptional control of a promoter with which it is not naturally associated. The promoter is maintained in an inactive state until it is desirable to release plasmid copy number from control at which point the promoter is activated so that transcription through the centromere sequence prevents the sequence from blocking separation of replicated plasmid strands.

In general, an exogenous structural gene may be placed immediately downstream of an endogenous promoter (i.e., a promoter which is native to the type of host cell) in order to submit expression of the exogenous gene to the control mechanism of the endogenous promoter. After placing a transcription terminator immediately downstream of the structural gene, the promoter-exogenous-gene-terminator construct may be inserted into a plasmid vector. A host cell transformed with the plasmid vector containing the construct may then be induced to express the exogenous gene under conditions which activate the promoter.

Among the endogenous promoters which may be employed to express exogenous genes is the promoter of the glyceraldehyde-3-phosphate dehydrogenase (GPD) gene of the yeast *S. cerevisiae.* In conjunction with a phosphoglycerate kinase (PGK) terminator, the GPD promoter may be used to express a structural gene encoding consensus interferon or a structural gene encoding hepatitis B surface antigen structural gene in *S. cerevisiae.* Bitter, et al., *Gene,* 32, 263-274 (1984).

Another approach to the expression of exogenous genes takes advantage of a yeast cell system for secreting a protein called mating factor $\alpha$ (MF$\alpha$). When secreted by cells of a mating type "$\alpha$", MF$\alpha$ acts to facilitate mating with cells of a so-called mating type "a". A series of MF$\alpha$ structural genes, linked together but separated by spacers, is preceded by a signal sequence which codes for a "signal" peptide. The signal peptide is translated as a part of MF$\alpha$ and enables MF$\alpha$ to be secreted, but the signal peptide is cleaved from MF$\alpha$ before secretion is completed. Attachment of the signal peptide to a foreign protein may be accomplished by substituting a gene encoding the foreign protein for one or more of the MF$\alpha$ genes. Such a manipulation results in a construct which may be used to obtain secretion of the foreign protein. Bitter, European Patent Application No. 123,294.

In still another approach to the expression of an exogenous gene under the control of a promoter which is not naturally associated with the gene, the promoter of the copper chelatin gene (also known as the copper metallothionein gene) may be used to confer copper inducibility upon a foreign gene. For example, when inserted into a plasmid between the copper chelatin promoter and the terminator from the yeast CYC1 gene, the *E. coli* galactokinase structural gene is rendered inducible by copper Butt et al., *Proc. Natl. Acad. Sci.* (USA), 81, 3332-3336 (1984); Butt, European Patent Application No. 134,773.

One approach to selecting cells containing an exogenous gene involves linking the exogenous gene with a gene which confers resistance to an antibiotic. Culturing cells to be screened in a medium containing the antibiotic will select for the cells containing the gene conferring resistance and, hence, for cells containing the exogenous gene. G418 is a 2-deoxystreptamine antibiotic which is structurally related to the antibiotic gentamycin but which has inhibitory activity against a wider variety of prokaryotic and eukaryotic organisms. A bacterial plasmid pAO43 contains a segment encoding aminoglycoside phosphotransferase-3' (I), which phosphorylates and thus inactivates several aminoglycoside antibiotics including G418. Transformation of yeast cells with a yeast-bacterial plasmid containing this segment (referred to herein as a $G418^R$ segment) confers G418 resistance upon the yeast cells. Jimenez, et al., *Nature,* 287, 869-871 (1980).

In the embodiment of the present invention described in the Examples, a basic plasmid, designated pap736, contains a $G418^R$ segment under the transcriptional control of the constitutive PGK promoter ($PGK_p$), a trp1 selection region, a yeast ars1 replication region, and DNA from the plasmid pBR322 which runs from an EcoRI site to a ClaI site. A hybrid centromere construction, $cup_p$-CEN3-$cup_t$ (a "cupomere"), is also present on the plasmid. The "cup" promoter ($cup_p$) and the "cup" terminator ($cup_t$) are derived from a 700 basepair yeast cup1 gene by creating a 209 basepair deletion in CUP1 by site-directed mutagenesis. The result of site-directed mutagenesis is a 460 basepair fragment containing a BglII site between $cup_p$ and $cup_t$. In order to complete construction of the cupomere, a 627 basepair Sau3A fragment containing a CEN3 segment is inserted into the BglII site so that a HincII site is located 477 basepairs from the $cup_p$ segment. A plasmid containing a cupomere is referred to herein as a "cupomere plasmid."

The G418-resistance segment includes a 0.7 kilobase region of the PGK promoter and a 1.5 kilobase BglII-BamHI fragment of a Tn5 transposon which contains a region encoding neomycin phosphotransferase. While cells in the single copy state are sensitive to G418, the G418-resistance segment provides for a $G418^R$ phenotype in 400 μg of G418 per ml when several copies of a plasmid containing this segment are present per cell. Therefore, this segment also provides a hitherto unrecognized selective means for isolating yeast cells having multiple copies of a plasmid.

Aberration of the basic plasmid was not observed to occur after amplification to the $G418^R$ multicopy state. Plasmids rescued from the multicopy state and reintroduced into yeast did not render the transformants resistant to G418 as would be expected if CEN3 deletions or alterations in the expession of G418 resistance had occurred. The clones into which the plasmids were reintroduced had to be taken through the same $CuSO_4$ and drug selection procedures originally performed in order to make them phenotypically $G418^R$.

Plasmids which have been constructed according to the present invention contain various systems for the expression of human erythropoietin (EPO). One system employs an α-factor promoter and has been designated pCOM(Scepo). Another plasmid construction, designated pap100, employs a GPD-hybrid promotor. Both constructions associate the α-factor signal with the EPO structural gene so that EPO may be secreted into a medium in which yeast cells containing the plasmids are cultured.

Plasmids pap100 and pCOM(Scepo) were transformed into a yeast strain YSDP4 (α, trp1, $CAN^R$, pep 4-3, CUP1). This strain is of mating type α and contains a tryptophan marker selection system, a segment for resistance to canavanine, a defect in cellular proteases, and a gene which confers resistance to $CuSO_4$. After selection of transformants, single colonies of each transformant were grown on minimal medium containing 0.5 mM $CuSO_4$ and then were transferred to YPD plates containing 400 μg of G418 per ml. $G418^R$ clones appeared at a frequency of $10^{-3}$ to $10^{-4}$. These clones were purified on G418-YPD plates. Transformants not grown on G418 were found to be in the single copy state while transformants grown on G418 were in the multicopy state.

The copy number of the plasmids in the single and multicopy state has been determined to be as indicated in Table I. For both pap100 and pCOM(Scepo), the plasmids are present at a number between 7 and 10 in the multicopy state.

TABLE I

| | State | Copy Number |
|---|---|---|
| pap100 | single | 1 |
| | multicopy | 7 |
| pCOM(Scepo) | single | 1 |
| | multicopy | 10 |

Although EPO secretion was observed to be higher in the single copy state of pCOM(Scepo), expression of the single copy state was as high as has been obtained using the same promotor system in a 2μ-derived vector. The 2μ vector segregates so that only about 30 percent of cultured cells have the plasmid. The stability of the cupomere plasmid is superior to that of the 2μ plasmid such that 99 percent of cells in culture have the cupomere plasmid in either the single or multicopy state.

In addition, galactose-induced expression of EPO in the pap100 cupomere plasmid provided the highest reported levels of secreted EPO obtained in yeast. A value as high as 280 μg per OD-L of EPO has been obtained in the pap100 system. EPO expression for pap100 and pCOM(Scepo), as determined by radioimmunoassay (RIA), is given in Table II in which the medium is YNB/CAA (Yeast Nitrogen Base (Difco, Detroit, Mich.) containing ½% casamino acids) including either 2% glucose or 2% galactose.

TABLE II

| | State | Medium | EPO μg/OD-L | |
|---|---|---|---|---|
| pCom(Scepo) | Single | SD/CAA | 48 ± 9 | 150 ± 65 |
| | Multicopy | +glucose | 6.1 | 53.8 ± 11.6 |
| pap100 | Single | SD/CAA | 1.5 | |
| | Multicopy | +glucose | 3.0 | |
| | Single | SD/CAA | 200 ± 5.5 | |
| | Multicopy | +galactose | 240± 16 | |

A Western blot analysis of samples of medium, according to the procedures of Burnette, *Anal. Biochem.*, 112, 195–203 (1981) and Hohmann, et al., *Virology*, 125, 432–444 (1983), confirmed galactose induction of EPO synthesis and a slightly higher production of EPO in the multicopy state of pap100. This higher production is more apparent at basal glucose levels.

As indicated in Table III the pap100 plasmids in the single copy state were found to be stable when grown in tryptophan-deficient medium even when high levels of expression in galactose were obtained. On the other hand, the multicopy state of pap100 was observed to be unstable in galactose, as demonstrated by a drop in the percentage of G418 resistant cells to 50 percent, although 95% of the cells were still $Trp^+$(indicating that the plasmid was still present albeit at the single copy level). Both pap100 and pCOM(Scepo) were observed to be stable in glucose.

TABLE III

| | State | Additions | % $Trp^+$ | % $G418^R$ |
|---|---|---|---|---|
| pap100 | single | glucose | 97 | — |
| | single | galactose | 100 | — |
| pap100 | multicopy | glucose | 100 | 99 |
| | multicopy | galactose | 100 | 52 |
| pCOM(Scepo) | single | glucose | 99 | — |
| | multicopy | glucose | 100 | 99 |

A Northern blot analysis [Thomas, *Proc. Natl. Acad. Sci.* (USA), 77, 5201–5205 (1981)] of the amount of EPO mRNA revealed five times as much EPO mRNA in the multicopy state as in the single copy state during growth on galactose. This result is consistent with the independently determined plasmid copy number of about 7.

By following the slope at steady state of the snythesis of EPO vs. cell growth, the differential rate of EPO synthesis was determined to be 591 for the multicopy state and 160 for the single copy state, a 3.7-fold difference. Thus, the similar final accumulation of secreted EPO in both states may be explained as being due to the fact that the single copy culture continued to grow for at least one more generation than did the multicopy state. However, the rate of EPO accumulation slowed down considerably during this continued growth.

The above-described experiments and results are described in greater detail in the following examples. In Example 1, the construction of plasmids having the G418 selection system and the transcriptionally controlled CEN system according to the present invention is described. Example 2 illustrates the operation of the G418 single copy/multicopy selection amplification system according to the present invention. In Example 3, the dependence of plasmid amplification upon transcriptional inactivation of the centromere function is demonstrated. In Example 4, the construction of an EPO vector from the basic plasmid of Example 1 and the MFα promoter system is described. In Example 5, the construction of pap100 is described. Example 6 discloses the clonal stability of pap100 plasmids in the multicopy state. In Example 7, the combined effects of the transcriptionally controlled centromere system and the G418$^R$ selection system upon EPO expression are examined. In Example 8 the plasmid stability of single- and multi-copy states of pap100 and pCOM(Scepo) are compared. Example 9 details the results of examinations of EPO gene expression obtained from cells containing the cupomere construction according to the present invention.

EXAMPLE 1

Figure 1:
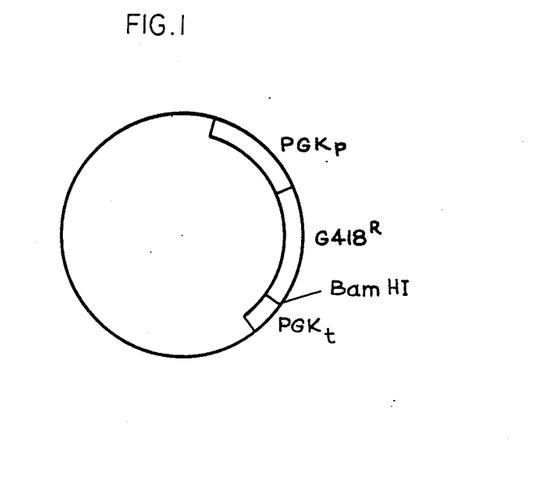
FIG. 1 is a partial restriction map of the plasmid pap12BD.
Figure 2:
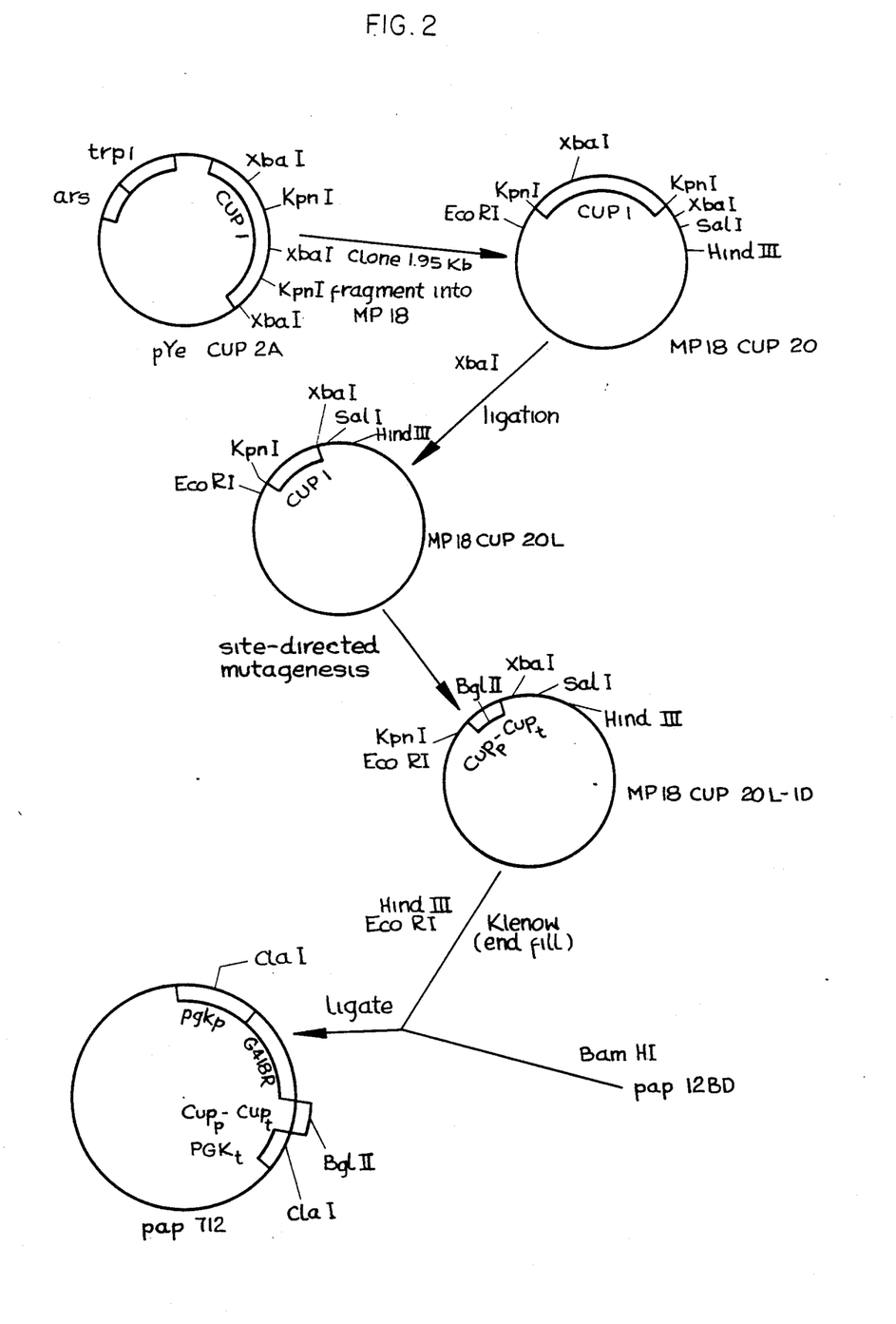
FIG. 2 illustrates construction of the plasmid pap712.
Figure 3:
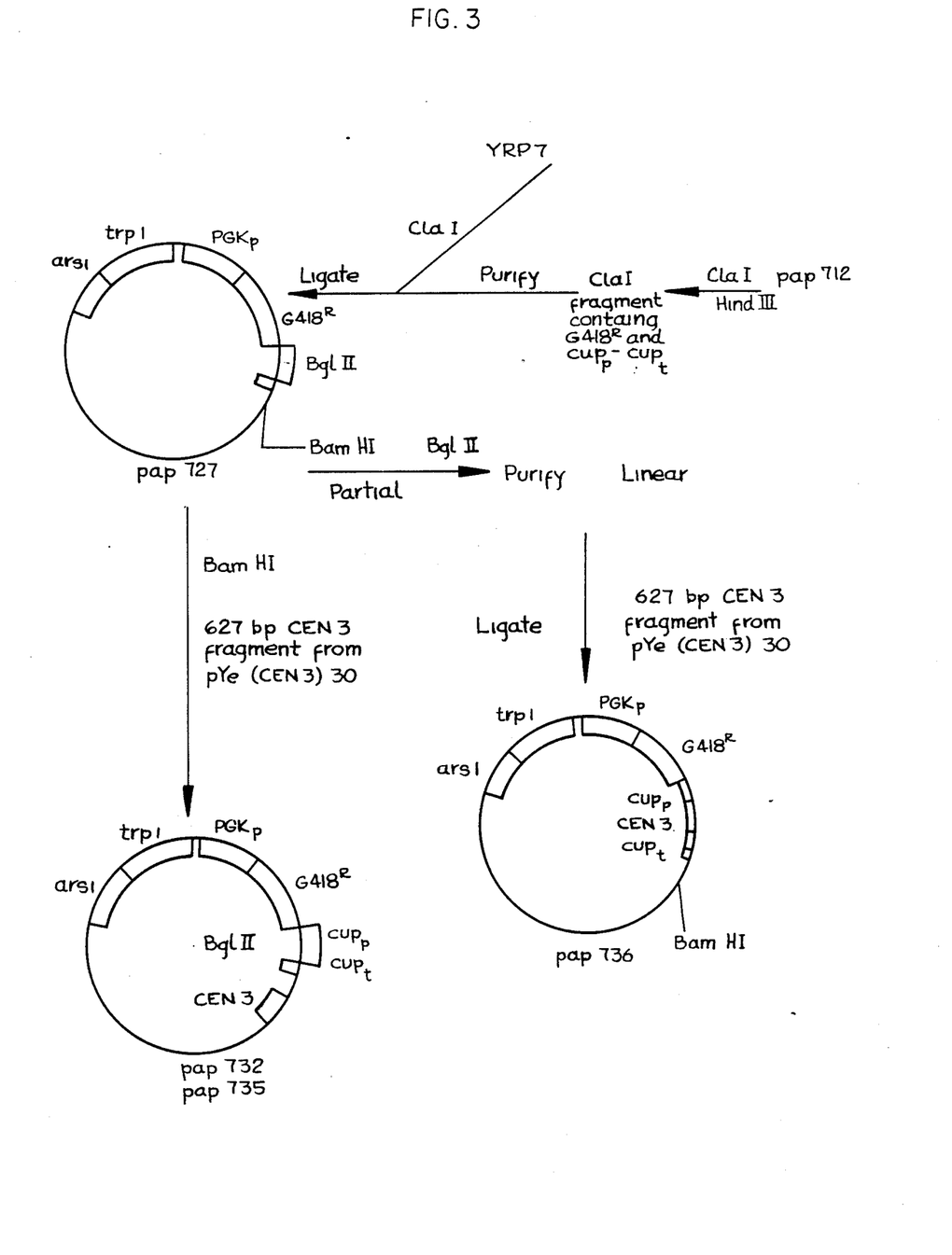
FIG. 3 illustrates construction of the plasmids pap732, pap735 and pap736.

The basic cupomere plasmid, pap736, was constructed as illustrated in FIGS. 2 and 3 from the plasmid pap12BD, a partial restriction map of which is illustrated in FIG. 1, and from the phage vector MP18CUP10L-10. The plasmid pap12BD, as illustrated in FIG. 1, was deposited with the American Type Culture Collection (ATCC), 12301 Parklawn Drive, Rockville, Md 20852, as Deposit No. 53231 on Aug. 13, 1985.

Construction of MP18CUP20

In order to delete a copper chelatin structural gene from an isolated CUP1 gene, a 1.95 kilobase KpnI fragment from the plasmid pYeCUP2A [deposited on August 13, 1985 with the American Type Culture Collection, 12301 Parklawn Drive, Rockville, Maryland 20852 as Deposit No. 53233] was ligated with a KpnI digested replication form (RF) of the DNA phage mP18 [Yanisch-Perron, et al., Gene, 33, 105–119 (1982)] to produce a phage designated MP18CUP20.

As illustrated in FIG. 2, among larger fragments, XbaI digestion of MP18CUP20 produced a 1.25 kilobase fragment and a larger phage fragment. The larger phage fragment was self-ligated and resulting RF phage preparations were screened using EcoRI and SalI digestion. Preparations designated MP18CUP20L contained a 0.7 kilobase EcoRI/SalI fragment as opposed to an 1.95 kilobase fragment as found in MP18CUP20.

A synthetic primer, designated pmCUP and having the sequence,

5' CAATCATCACATAA<u>AGATCT</u>AACTATTTGCTG 3'
                           BglII was constructed according to the procedures of Carruthers, et al., U.S. Pat. No. 4,415,732. Site-directed mutagenesis of MP18CUP20L employing pmCUP according to the method of Zoller, et al., Methods in Enzymology, 100, 468–500 (1983), resulted in deletion of the copper chelatin structural gene and in creation of a BglII site between the copper chelatin upstream (promoter) cup$_p$ and downstream (terminator) cup$_t$ flanking regions. Table IV illustrates the sequence of a single strand of the copper chelatin gene and its upstream and downstream flanking regions with the deleted region being indicated by underlining.

TABLE IV

| AGAGATT | | | | | |
|---|---|---|---|---|---|
| CTTTTGCTGG | CATTTCTTCT | AGAAGCAAAA | AGAGCGATGC | GTCTTTTCCG | CTGA |
| ACCGTTCCAG | CAAAAAAGAC | TACCAACGCA | ATATGGATTG | TCAGAATCAT | AT |
| AAAAGAGAAG | CAAATAACTC | CTTGTCTTGT | ATCAATTGCA | TTATAATATC | TTCT |
| TGTTAGTGCA | ATATCATATA | GAAGTCATCG | AAATAGATAT | TAAGAAAAAC | AAAC |
| TGTACAATCA | ATCAATCAAT | CATCACATAA | AATGTTCAGC | GAATTAATTA | ACTTCCAAAA |
| GAAGGTCATG | AGTGCCAATG | CCAATGTGGT | AGCTGCAAAA | ATAATGAACA | ATGCCAA |
| <u>AAATCATCTA</u> | <u>GCTGCCAACG</u> | <u>GGGTGTACAG</u> | <u>CGACGACAAA</u> | <u>TGCCCTGCGG</u> | <u>TAAC</u> |
| <u>AAGTCTGAAG</u> | <u>AAACCAAGAA</u> | <u>GTCATGCTGC</u> | <u>TCTGGGAAAT</u> | <u>GAAACGAATA</u> | <u>GTCTTT</u> |
| <u>AATATATTGA</u> | TCTAACTATT | TGCTGTTTTT | AATTTTTAAA | AGGAGAAGGA | AGTTTAA |
| TCGACGATTC | TACTCAGTTT | GAGTACACTT | ATGTATTTTG | TTTAGATACT | TTGTT |
| AATTTATAGG | TATACGTTAA | TAATTAAGAA | AAGGAAATAA | AGTATCTCCA | TATC |
| TCGCCCCAAG | AATAAAATAT | TATTACCAAA | TTCTACTTTG | CCTAACTTAC | AACTCTG |
| TATAGAATCC | CCAGATTTCG | AATAAAAAAA | AAAAAAAAAG | CT | |

A partial restriction map of the resulting vector designated MP18CUP20L-1D, is illustrated in FIG. 2. In this vector, the cup$_p$-cup$_t$ sequence is given in Table V wherein a BglII site is indicated by underlining.

TABLE V

| TCTAGAAGCA | AAAAGAGGGA | TGCGTCTTTT | CCGCTGA | | |
|---|---|---|---|---|---|
| ACCGTTCCAG | CAAAAAAGAC | TACCAACGCA | ATATGGATTC | TCAGAATCAT | AT |
| AAAAGAGAAG | CAAATAACTC | CTTGTCTTCT | ATCAATTGCA | TTATAATATC | TTCT |
| TGTTAGTGCA | ATATCATATA | GAAGTCATCG | AAATAGATAT | TAAGAAAAAC | AAAC |
| TGTACAATCA | ATCAATCAAT | CATCACATAA | <u>A</u> | | |
| <u>GATCT</u>AACTA | TTTGCTGTTT | TTAATTTTTA | AAAGGAGAAG | GAAGTTTAA | |
| TCGACGATTC | TACTCAGTTT | GACTACACTT | ATGTATTTTG | TTTAGATACT | TTGTT |
| AATTTATAGG | TATACGTTAA | TAATTAAGAA | AAGGAAATAA | AGTATCTCCA | TATG |
| TCGCCCCAAG | AATAAAATAT | TATTACCAAA | TTCTAGTTTG | CCTAACTTAC | AACTCTG |
| TATAGAATCC | CCAGATTTCG | AATAAAAAAA | AAAAAAAAAG | CT | |

As further illustrated in FIG. 2, the replicative form (RF) of MP18CUP20L-1D was digested with HindIII and EcoRi restriction enzymes to provide a fragment which was end-filled using the Klenow fragment of DNA polymerase and all four nucleoside triphosphates to obtain a cup$_p$-cup$_t$ insert for pap12BD.

Pap12BD was then digested with BamHI. BamHI-cut pap12BD DNA was end-filled using Klenow fragment and all four nucleoside triphosphates. Purified EcoRI-HindIII, end-filled restriction fragment of MP18CUP20L-1D DNA was ligated to purified pap12BD DNA overnight and the ligation products were used to transform an *E. coli* strain K12 and a clone was found having a plasmid designated pap712. A partial restriction map of pap712, the ligation product of the MP18CUP20L-1D restriction fragment and pap12BD, is illustrated in FIG. 2. In pap712 the $cup_p$-$cup_t$ fragment is inserted into pap12BD after the G418$^R$ segment and between the PGK promoter and PGK terminator of pap12BD.

Construction of Pap727

As illustrated in FIG. 3, a sample of pap712 DNA was digested with ClaI and HindIII. The reaction mixture was run on a gel overnight. After ethidium bromide staining, the gel was examined under ultraviolet light and a 3 kilobase band was excised and collected into a tube. The agarose gel was melted, diluted and extracted to provide a pap712 DNA ClaI fragment which was concentrated and purified.

YRP7 DNA [Tschumper, et al., *Gene*, 10, 157–166 (1980)] was digested with ClaI enzyme. Complete digestion was verified on a mini-gel. The 3 kilobase ClaI restriction fragment of pap712 and the ClaI restriction fragment of YRP7 were ligated using T4 DNA ligase. Successful ligation was confirmed on a mini-gel.

Screening for plasmids

*E. Coli* strain JA300 (A.T.C.C. No. 33588) (Tschumper, supra) was transformed with the ligation products of the YRP7 ClaI restriction fragment and the pap712 ClaI restriction fragment according to the procedure of Hanahan, *J. Mol. Biol.*, 166, 559–580 (1983). Plasmid minipreps were prepared by a standard alkali SDS plasmid preparation from the transformed clones. A 25 μl sample was loaded on a 0.8% gel and run overnight. The plasmid pap727, a partial restriction map of which is illustrated in FIG. 3, was identified in one of the clones on the basis of an analysis of the gel.

Construction of pap736

Pap727 DNA was digested with BglII restriction enzyme. Aliquots were removed and treated with a stop buffer. All of the aliquots were examined by gel electrophoresis (0.6% Tris-borate gel). Bands identified as partial digests underwent low melting agarose DNA purification.

The partial BglII digest of pap727, 627 bp fragment of CEN3 [Fitzgerald-Hayes, et al., *Cell*, 29, 235–244 (1982)] from a plasmid pYe(CEN3)30 [deposited with the American type Culture Collection, 12301 Parklawn Drive, Rockville, Maryland 20852 as Deposit No. 53232 on Aug. 13, 1985] were ligated with T4 ligase as above. *E. coli* strain JA300 was transformed by the Hanahan procedure with 200 ng of the ligation mixture. Hanahan, supra. Clones were innoculated into L broth plus 50 μg/ml ampicillin and 50 μg/ml thymidine.

Cells were centrifuged out of 1 ml of broth. Plasmids were prepared by the alkali SDS procedure as above. Orientations of inserts were determined from digests. A plasmid designated pap736 was selected as the basic cupomere plasmid on the basis of the results of agarose gel electrophoresis of these digests.

Transformation of yeast cells

Cells of yeast strain J17 [Fitzgerald-Hayes, et al. *Cell*, 29, 235–244 (1982)] were transformed with plasmid pap736 according to the lithium acetate procedure of Kuo, et al., *Mol. Cell. Biol.*, 3, 1730–1777 (1983). Trp+ transformants were selected on YNB/CAA/ura/ade/-glu, i.e., Yeast Nitrogen Base (YNB, available from Difco, Detroit, Michigan), containing 0.5% casamino acids (CAA), 10 μg/ml uracil (ura), 10 μg/ml adenine sulfate (ade) and 2% glucose (glu).

Preparation of pap732 and pap735

Pap727 DNA was digested with BamHI. Complete digestion was verified on a minigel. The BamHI-cut pap727 DNA and the 627 bp CEN3 fragment from pYe(CEN3)30 were ligated by T4 ligase as described above. Cells of *E. coli* strain JA300 were transformed by the Hanahan procedure as above. Twenty transformed clones were innoculated into L broth containing 50 μg/ml of ampicillin and 50 μg/ml of thymidine. The innoculated clones were incubated overnight. Plasmids were prepared from the incubated clones by the standard alkali SDS procedure.

On the basis of SalI, BamHI/SalI and HincII digests of the plasmids, plasmids designated pap732 and pap735 were determined to have a CEN3 sequence in a position and orientation relative to the $cup_p$-$cup_t$ insert as shown in FIG. 3.

EXAMPLE 2

Induction of the multi-copy state

A clone of yeast strain J17 containing pap 736 was taken from the transformation plate and streaked on a plate containing YNB/CAA/ura/ade/glu/CuSO$_4$ (i.e., YNB/CAA/ura/ade/glu and 0.5 mM CuSO$_4$). The plate was incubated for 2 days at 30° C. On the third day, a single isolated colony was taken from the plate and streaked onto a new plate of the same composition. After 4 more such transfers, a single colony was taken from the fifth plate and streaked on four plates containing YPD plus G418 at the respective concentrations of 400 μg per ml, 500 μg per ml, 600 μg per ml and 700 μg per ml. These plates were incubated at 30° C. for 2 days. Five serial transfers were made on YNB-/CAA/ura/ade/glu plates (i.e., YNB/CAA/ura/ade/-glu/CuSO$_4$ plates without CuSO$_4$) and a single colony taken from the fifth transfer plate was streaked onto four plates containing YPD plus G418 (at the respective concentrations of 400 μg per ml, 500 μg per ml, 600 μg per ml and 700 μg per ml).

Cells which had been grown on CuSO$_4$ grew on all four concentrations of G418 while cells taken from plates without CuSO$_4$ did not grow on any plate to a significant degree (a few small colonies were found upon 4 days of incubation in the plate containing the lowest concentration of G418). This outcome indicated that induction by CuSO$_4$ increased G418 resistance, presumably as a result of an increase in G418-containing plasmid copy number.

A colony taken from the second transfer plate grew on all four concentrations of G418. This clone was designated Series A. A Series A clone streaked on another set of G418 plates at the same concentrations was designated Series B. Colonies of both cells grew on plates without tryptophan indicating the presence of pap736 plasmid.

Stability of pap736 and pap736 Series A and Series B

Figure 4:
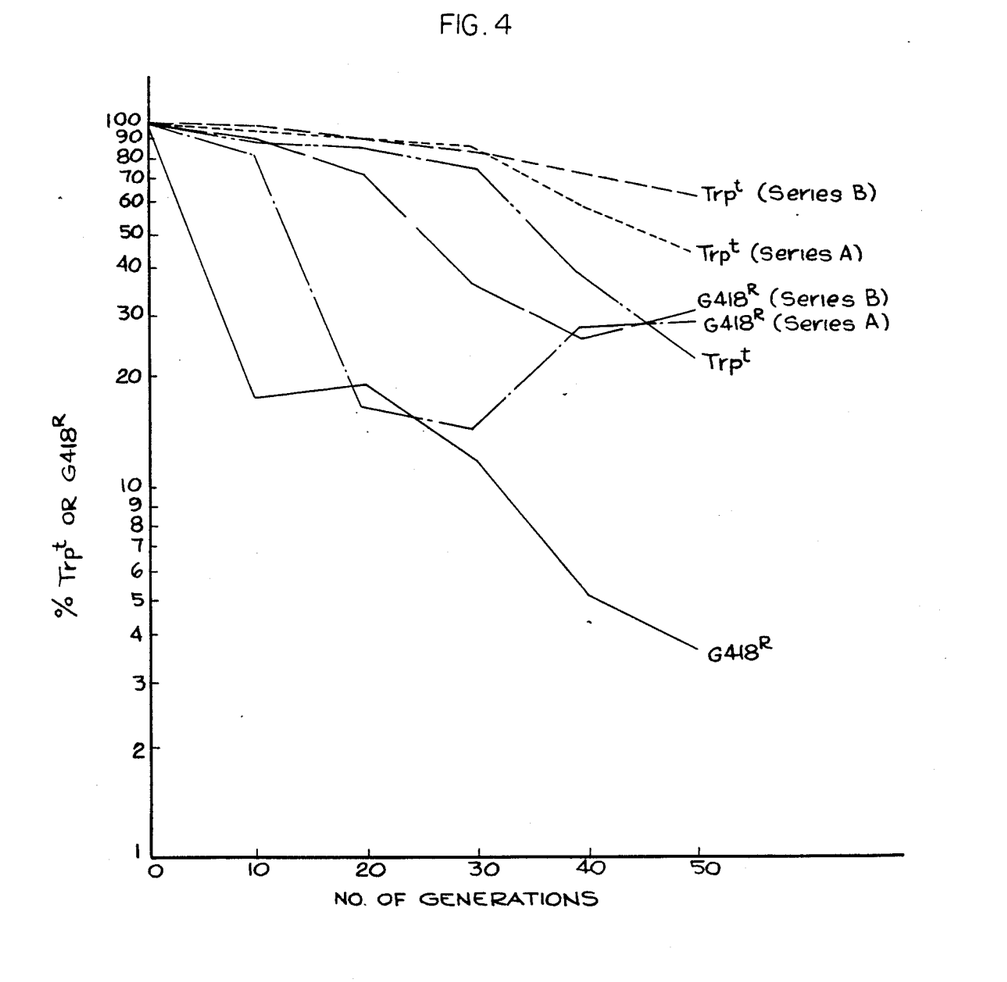
FIG. 4 graphically depicts the stability of plasmids containing the tryptophan and G418 resistance markers.

Samples from serial cultures of pap736, pap736 Series A, and pap736 Series B were grown on YNB/CAA/glu/ura/ade/trp (i.e., YNB/CAA/glu/ura/ade containing 0.01% tryptophan) plates and cell counts were obtained. On the basis of these counts, dilutions were made to obtain $10^6$ cell for innoculation into YPD broth and the dilutions were grown for ten generations therein. The dilutions of the culture were plated onto YNB/CAA/ura/ade/glu/trp. The cultures were replica plated on YNB/CAA/ura/ade/glu plates without tryptophan and on these plates with 400 μg per ml of G418. The plates were incubated at 30° C. for 3 days and the process was repeated for 40 more generations. The results of an examination for the stability of plasmids containing the tryptohan marker and for G418 resistance are shown in Table VI and in FIG. 4.

TABLE VI

| | Total No. of Colonies | Trp+ | Trp− | $G418^R$ | $G418^S$ | % Trp+ | % G418R |
|---|---|---|---|---|---|---|---|
| pap736 (Single copy) | | | | | | | |
| 10 gen | 420 | 375 | 45 | 72 | 348 | 89.0 | 17.0 |
| 20 gen | 200 | 166 | 34 | 37 | 163 | 83.0 | 18.0 |
| 30 gen | 480 | 360 | 120 | 60 | 420 | 75.0 | 12.5 |
| 40 gen | 480 | 178 | 302 | 25 | 455 | 37.0 | 5.2 |
| 50 gen | 210 | 50 | 160 | 6 | 204 | 23.0 | 2.8 |
| A4 (Multi copy) | | | | | | | |
| 10 gen | 460 | 458 | 2 | 380 | 80 | 99.5 | 82.6 |
| 20 gen | 360 | 334 | 26 | 63 | 297 | 92.7 | 17.0 |
| 30 gen | 400 | 340 | 60 | 127 | 363 | 85.0 | 15.0 |
| 40 gen | 185 | 111 | 74 | 50 | 135 | 60.0 | 27.0 |
| 50 gen | 270 | 120 | 250 | 36 | 234 | 44.0 | 29.0 |
| B4 (Multi copy) | | | | | | | |
| 10 gen | 500 | 496 | 5 | 452 | 48 | 99.2 | 90.9 |
| 20 gen | 280 | 266 | 14 | 232 | 48 | 95.0 | 82.0 |
| 30 gen | 600 | 492 | 108 | 220 | 380 | 82.0 | 36.0 |
| 40 gen | 347 | 250 | 97 | 89 | 258 | 72.0 | 25.6 |
| 50 gen | 350 | 230 | 120 | 110 | 240 | 65.0 | 31.0 |

A similar examination of strain J17 containing pap732 for the presence of the tryptophan marker revealed results as shown in Table VII.

TABLE VII

| No. of Generations | Total No. of Colonies | Trp+ | % Trp |
|---|---|---|---|
| 10 gen. | 153 | 132 | 86.2 |
| 20 gen. | 262 | 122 | 46.5 |

The results of these generational studies indicate that there is enhanced stability of a plasmid, such as the plasmid pap736, containing a transcriptionally-controlled centromere, such as the cupomere, in a single or a multicopy state over an ordinary centromere containing plasmid, such as pap732. Furthermore, the multicopy state is even more stable than the single copy state. These conclusions are based on the examination of the Trp+ behavior inasmuch as even one copy of plasmid renders the cell Trp+.

In the case of $G418^R$, there is also an enhanced stability especially in the multicopy state. In the above experiment, a higher frequency of $G418^R$ in a single copy state was seen then, for example, in Table VIII, infra. However, there is still reduced stability when compared to the multicopy state. The $G418^R$ does disappear more quickly than the Trp+ character because the former one is dependent upon the presence of many copies of plasmid rather than just one.

Southern Blot of pap727, pap736 (single copy), Series A and Series B

A copy number experiment [i.e., a Southern blot experiment according to Southern, *J. Mol. Biol.*, 98, 503–517 (1975)] was performed upon the Series A and Series B as well as upon pap736 and pap727. The result was that in the series A and B both $G418^R$ clones resistant to 400 μg G418/ml have a copy number of 7 per cell while the ones resistant to higher concentrations have copy numbers of 4. The single copy pap736 has a copy number of one per cell while pap727 has a copy number of about 10 per cell.

Back transformation of multi copy plasmids was accomplished by isolation of DNA from each of pap736 (single copy) and Series A and Series B clones. Cells were grown in YNB/CAA/glu/ade/ura up to saturation. The cells were centrifuged and resuspended in 5 ml sorbitol. Zymolyase (Kirin, Tokyo, Japan) was added to the resuspended cells. The cells were incubated until protoplasted. Protoplasts were centrifuged, washed and resuspended in lysis buffer (4% SDS; 10mM Tris pH 7.4; and 10mM EDTA). DNA was extracted from the protoplasts by standard techniques.

The original plasmids were back transformed into *E. coli* strain RR1 (A.T.C.C. No. 31343) resistant transformants were obtained and these clones were screened for the presence of the original plasmid. From each sample, 5 μl of plasmid DNA was digested with BamHI and SalI with the expectation of obtaining the following pieces: a 0.275 kilobase pBR322 fragment; a 0.400 kilobase G418 fragment; a 1.78 kilobase centromere fragment; and a 7.3 kilobase fragment containing the remainder of plasmid YRP7. All of the clones analyzed have these fragments which indicates that no aberration of the original plasmid pap736 occurred during the process of amplification to the multicopy state.

The DNA was transformed into yeast strain J17 by the lithium acetate procedure of Kuo, et al., supra. Cells derived from transformation with minipreps of pap736 (single copy), Series A and Series B were plated on SD/CAA/glu/ade/ura plates at 30° C. for 2 to 3 days. Three colonies were taken from each plate and streaked on a YPD plate and a YPD plate+400 μg per ml G418. These plates were incubated for 2 to 3 days at 30° C. with the result that all cells were sensitive to G418 at the 400 μg per ml level after 2 days, confirming that centromere was still functional.

EXAMPLE 3

Demonstration of plasmid amplification dependence on transcriptional inactivation of the centromere function J17 cells respectively containing plasmids pap727, pap732, pap735 or pap736 were streaked onto SD/CAA/ade/ura plates with or without 1 mM CuSO4. Single colonies derived from each type of plasmid were resuspended in water and then plated onto a separate YPD plate containing 400 μg per ml of G418. Results of this procedure are listed in Table VIII.

dent upon induction with CuSO4, which indicates that transcription through the CEN3 sequence is required for amplification.

EXAMPLE 4

A sequence for a manufactured structural gene encoding the human species EPO sequence and incorporating, preference codons for expression in yeast (S. cerevisiae) cells (i.e., a "Scepo" sequence) according to Lin, PCT Application No. WO 85 02610 (incorporated by reference herein) is given in Table IX. The manufacturing protocol for this gene was set forth in Alton, et al. PCT Application No. WO 83/04053 (incorporated by reference herein).

TABLE IX
SCEPO GENE

```
            -1 +1
HindIII     ArgAla
AGCTTGGATA  AAAGAGCTCC  ACCAAGATTG  ATCTGTGACT  CGAGAGTTTT
   ACCTAT   TTTCTCGAGG  TGGTTCTAAC  TAGACACTGA  GCTCTCAAAA GGAAAGATAC  TTGTTGGAAG  CTAAAGAAGC  TGAAAACATC  ACCACTGGTT
CCTTTCTATG  AACAACCTTC  GATTTCTTCG  ACTTTTGTAG  TGGTGACCAA GTGCTGAACA  CTGTTCTTTG  AACGAAAACA  TTACGGTACC  AGACACCAAG
CACGACTTGT  GACAAGAAAC  TTGCTTTTGT  AATGCCATGG  TCTGTGGTTC GTTAACTTCT  ACGCTTGGAA  ACGTATGGAA  GTTGGTCAAC  AAGCTGTTGA
CAATTGAAGA  TGCGAACCTT  TGCATACCTT  CAACCAGTTG  TTCGACAACT AGTTTGGCAA  GGTTTGGCCT  TGTTATCTGA  AGCTGTTTTG  AGAGGTCAAG
TCAAACCGTT  CCAAACCGGA  ACAATAGACT  TCGACAAAAC  TCTCCAGTTC CCTTGTTGGT  TAACTCTTCT  CAACCATGGG  AACCATTGCA  ATTGCACGTC
GGAACAACCA  ATTGAGAAGA  GTTGGTACCC  TTGGTAACGT  TAACGTGCAG GATAAAGCCG  TCTCTGGTTT  GAGATCTTTG  ACTACTTTGT  TGAGAGCTTT
CTATTTCGGC  AGAGACCAAA  CTCTAGAAAC  TGATGAAACA  ACTCTCGAAA GGGTGCTCAA  AAGGAAGCCA  TTTCCCCACC   AGACGCTGCT TCTGCCGCTC
CCCACGAGTT  TTCCTTCGGT  AAAGGGGTGG  TCTGCGACGA  AGACGGCGAG CATTGAGAAC  CATCACTGCT  GATACCTTCA  GAAAGTTATT  CAGAGTTTAC
GTAACTCTTG  GTAGTGACGA  CTATGGAAGT  CTTTCAATAA  GTCTCAAATG TCCAACTTCT  TGAGAGGTAA  ATTGAAGTTG  TACACCGGTG  AAGCCTGTAG
AGGTTGAAGA  ACTCTCCATT  TAACTTCAAC  ATGTGGCCAC  TTCGGACATC AACTGGTGAC  AGATAAGCCC  GACTGATAAC  AACAGTGTAG
TTGACCACTG  TCTATTCGGG  CTGACTATTG  TTGTCACATC

SALI
ATGTAACAAA  G
TACATTGTTT  CAGCT
```

TABLE VIII

|  | Pregrown in CuSO4 | % Cells with G418-Resistance |
|---|---|---|
| pap727 | No | 8.5 |
|  | Yes | 3.5 |
| pap732 | No | 0.00075 |
|  | Yes | <0.00016 |
| pap735 | No | 0.05 |
|  | Yes | 0.002 |
| pap736 | No | 0.007 |
|  | Yes | 0.7 |
| pap737 | No | 0.0013 |
|  | Yes | 0.007 |

Figure 5:
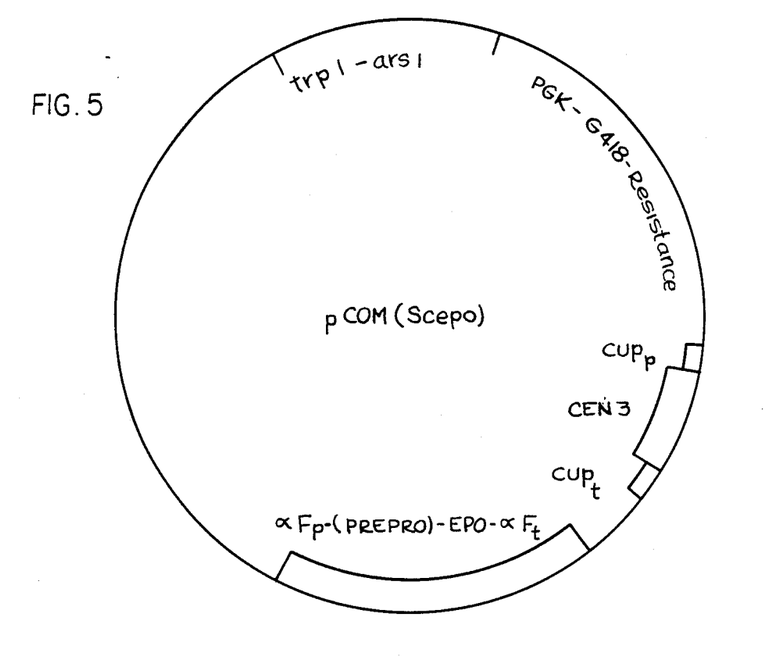
FIG. 5 is a partial restriction map of the plasmid pCOM(Scepo)

As indicated in Table VIII, amplification of the plasmid born G418 is dependent upon the CEN3 centromere sequence being inserted in the proper orientation next to the cup promoter. Amplification is also depen- The α-factor expression system for Scepo gene products is described in Bitter, European Patent Application 123,294 (incorporated by reference herein). In this system, DNA encoding the signal sequence of the yeast α-factor gene product is positioned immediately 5' to the coding region of the exogenous gene to be expressed. As a result, the translated gene product includes a signal sequence which is removed by an endogenous yeast enzyme during secretion. As noted in Table IX, the alanine (+1) codon is preceded by a linker sequence allowing for direct insertion into a plasmid including the first 80 residues of the α-factor leader following the α-factor promoter. The specific construction for Scepo sequence expression involved a ligation according to Alton, et al., supra, including the Scepo sequence as given in Table IX and the large fragment of HindIII/SalI digestion of a plasmid paC3 From the resulting plasmid paC3/Scepo, the α-factor promoter and leader sequence (i.e., the signal or pre pro sequence) and Scepo gene were isolated by digestion with BamHI and ligated into a BamHI digested plasmid pap736 to form expression plasmid pCOM(Scepo). pCOM(Scepo) is depicted in FIG. 5 wherein: αFP is the α-factor promoter; $\alpha^F$(prepro) is the prepro (i.e., signal) sequence of α-factor terminator.

Although pCOM(Scepo) was constructed as described above, it is clear to one skilled in the art that possession of the sequence of Table IX readily permits construction by manufacture of a synthetic gene and insertion of the gene into any suitable plasmid.

EXAMPLE 5

Construction of pap100

A plasmid GPD (αFEPO) contains a hybrid GPD promoter wherein an upstream activating sequence (UAS) is inserted at an AvaII site in the GPD portable promoter described in Bitter, et al., *Gene*, 32, 263–274 (1984). Specifically, the *S. cerevesiae* GPD portable promoter has been modified at an AvaII site by introduction of the upstream regulatory sequence $UAS_G$, which has been published in Johnston, et al., *Mol. Cell. Biol.*, 4, 1440–1448 (1984). The portion introduced is the portion between DdeI and sau3a restriction sites in the sequence of Johnston, et al., supra. The UAS is inserted upstream of a T A T A box homology of the portable promoter such that insertion of the UAS confers regulation upon the GPD promoter which is otherwise always turned on, i.e., a constitutive promoter. Expression is by growth in galactose. A low basal level of expression is observed.

Digestion of pGPD (αFEPO) first with ClaI followed by digestion with BamHI permitted isolation by the low melting agarose gel procedure of a 2.04 kb fragment which contains the hybrid GPD-gal promoter, the α-factor prepro region, the Scepo gene, and the α-factor terminator. Plasmid pap736 was cut with BamHI. Both this cut plasmid and the 2.04 kb fragment were end-filled by Klenow fragment in the presence of all four nucleoside triphosphates. These DNAs were then ligated (blunt end) by T4 ligase. Competent *E. coli* cells of strain RR1 were prepared by the procedure of Hanahan, supra and transformed with the products of the ligation.

Figure 6:
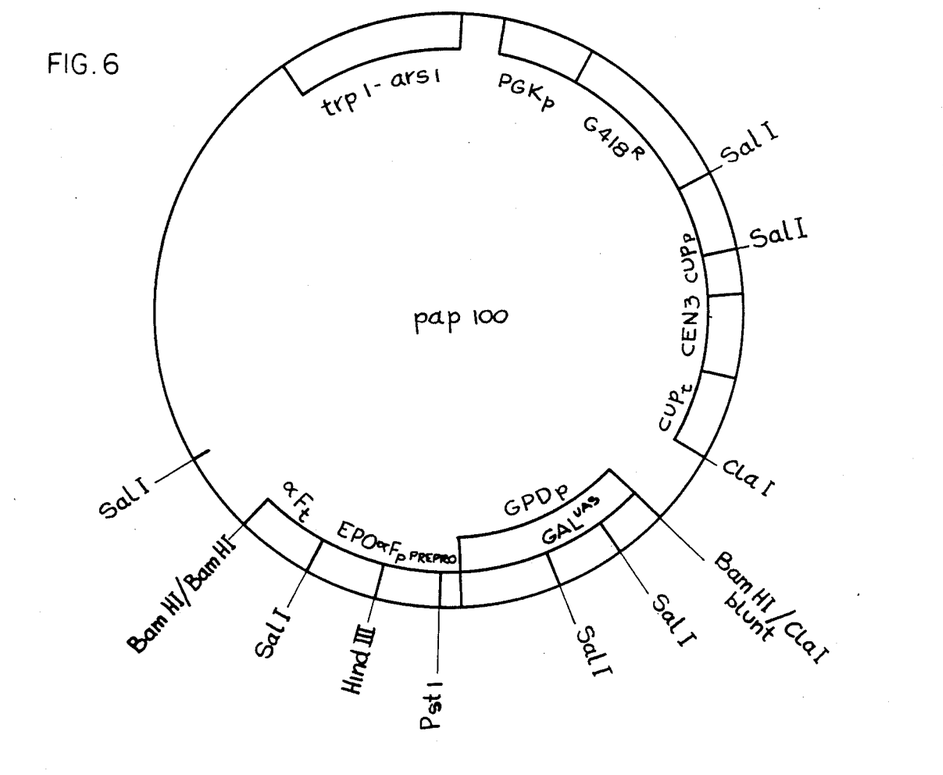
FIG. 6 is a partial restriction map of the plasmid pap100.

Forty colonies of transformed cells which were observed to be ampicillin-resistant in L-broth plus 50 μg/ml of ampicillin were innoculated and grown overnight. Next, samples of these cultures were centrifuged and plasmids were prepared by the standard alkali/SDS plasmid preparation procedure. Plasmid DNA was digested with HindIII and the digestion was analyzed on a 0.7% agarose gel. Because the pCOM(Scepo) insert has two HindIII sites and pap736 has 2 HindIII sites, pap736 plasmids containing the insert have 4 DNA bands upon HindIII digestion. A plasmid designated pap100 exhibited the expected four bands upon HindIII digestion. A partial restriction map of pap100 is illustrated in FIG. 6 wherein: GAL UAS indicates the upstream activating sequence of GAL1-GAL10 described above; and GPD promoter into which it is inserted.

Transformation of pap100 into yeast strain YSDP4.

The plasmid pap100 was transformed into the yeast strain YSDP4 (α, trp1, $CAN^R$, pep 4-3, CUP1) [deposited with the American Type Culture Collection, 12301 Parklawn Drive, Rockville, Md. 20852 as Deposit No. 20734] by the lithium acetate procedure of Kuo, et al., supra. Transformants were selected and single colonies of each transformant were grown on yeast minimal medium containing 0.5 mM CuSO4. Next, the colonies were transferred to YPD plates containing 400 μg of G418 per ml. $G418^R$ clones (multicopy state) were isolated.

Example 6

Clonal Stability of pap100 plasmids in multicopy state.

Eight colonies derived from a single clone of pap100-transformed YSDP4 cells which were grown on a G418 plate (i.e., $G418^R$) were innoculated into 5 ml of YPD broth (2% peptone; 1% yeast extract; and 2% glucose) and incubated overnight at 30° C. Next, the resulting cultures were diluted and replated onto YPD and onto a plate containing YPD plus G418 at a concentration of 400 μg per ml. These plates were incubated at 30° C. for 3 days, at the end of which time colonies were counted on both plates and the percentage of G418 resistance was calculated. The results of this calculation are shown in Table X.

TABLE X

| No. | Total No. of Colonies on YPD | Total No. of Colonies on G418 | % $G418^R$ |
|---|---|---|---|
| 1 | 28 | 15 | 53.5% |
| 2 | 38 | 9 | 23.6% |
| 3 | 19 | 18 | 94.7% |
| 4 | 53 | 2 | 3.7% |
| 5 | 57 | 49 | 85.95% |
| 6 | 60 | 4 | 6.6% |
| 7 | 81 | 37 | 45.6% |
| 8 | 58 | 21 | 36.2% |

Four colonies of each of clones 3 and 5, the clones which exhibited the highest percentage of G418 resistance, were suspended in 100 μl and 5 μl innoculated into 5 ml of YPD broth. After incubation overnight at 30° C., 100 μl of the culture was first diluted into 10 ml of H2O, and then 10 μl was taken from the first dilution and diluted into 100 μl ml. 50 μl of the resulting solution were plated on a YPD plate and on a YPD plate containing 400 μg/ml of G418. The plates were incubated at 30° C. with results as shown in Table XI.

TABLE XI

| No. | Total Colony on YPD | Colony on G400,GR | % $G418^R$ |
|---|---|---|---|
| 1 | 720 | 285 | 34.5% |
| 2 | 680 | 102 | 15.0% |
| 3 | 564 | 193 | 34.2% |
| 4 | 660 | 211 | 31.9% |
| 5 | 712 | 267 | 37.5% |
| 6 | 810 | 217 | 26.79% |
| 7 | 860 | 240 | 27.9% |
| 8 | 675 | 209 | 30.96% |

The results in Tables X and XI indicate that there is a clonal variation in the stability of the multicopy state of pap100, that is, the initially isolated $G418^R$ clone (Table XI) has a wide range of $G418^R$ stabilities after nonselective growth in YPD broth. This variability was also seen in Table VI when comparing A4 and B4 clones. When clones of the higher stability type were examined (Table XI) they had a more uniform range of stability.

Example 7

Determination of copy number.

Cells unamplified with respect to pap100 (pap100S), i.e., G418-sensitive, were grown on a YNB/glu/CAA plate. Cells amplified with respect to pap100 (pap100M), i.e., G418-resistant, were grown on a YPD plate containing 400 μg/ml G418. A single colony from each of the plates was innoculated in 100 ml of YNB-/CAA/glu/0.1% YE and incubated with shaking overnight at 30° C. Next, cells were separated from the medium by centrifugation and resuspended in SCE containing zymolyase (1 mg per ml) and 2%β-mercaptoethanol and incubated at 37° C. for ½ hour to obtain protoplasts. The protoplasts were washed, centrifuged and resuspended. DNA was extracted from the nuclei according to standard procedures.

Each plasmid type isolated according to this was digested with BglII. A 0.8% Tris-borate gel was prepared and a sample of each type was run on the gel overnight at 30 volts. A trp-ars fragment was isolated and labeled by nick translation Rigby, et al., *J. Mol. Biol.*, 113, 237 (1977) and employed in a southern blot procedure [Southern, *J. Mol. Biol.*, 98, 503–517 (1975)] to obtain the results as shown in Table XII in which chromosome bands are identified as "C-bands" and in which plasmid bands are identified at "P-bands".

TABLE XII

| | | | |
|---|---|---|---|
| pap100S | C-band (1) | 8,542 | 1 copy |
| | C-band (2) | 6,921 | |
| | Total | 15,461 | |
| | P-band (1) | 9,453 | 1 copy |
| | P-band (2) | 6,458 | |
| pap100M | Total | 15,911 | |
| | C-band (1) | 5,689 | 1 copy |
| | C-band (2) | 4,906 | |
| | Total | 10,595 | |
| | P-band (1) | 38,626 | 7.2 copies |
| | P-band (2) | 36,856 | |
| pCOM(Scepo)S | Total | 75,482 | |
| | C-band (1) | 2,960 | 1 copy |
| | C-band (2) | 1,772 | |
| | Total | 4,732 | |
| | P-band (1) | 3,731 | 1 copy |
| | P-(2) | 3,402 | |
| pCOM(Scepo)M | Total | 7,133 | |
| | C-band (1) | 1,903 | 1 copy |
| | C-band (2) | 1,594 | |
| | Total | 3,497 | |
| | P-bands 1 and 2 together | 35,174 | 10.6 copies |

These data show that when the $G418^R$ clones are selected for they become multicopy. That is, pCOM(-Scepo) has 7 copies per cell and pap100 has 10 copies per cell with respect to a yeast chromosome. As seen above with pap736 alone, 4 and 7 copies per cell were found in the multicopy state. Thus, insertion of the erythropoietin gene did not affect the amplification of the cupomere plasmid.

Example 8

Plasmid stability in yeast strain YSDP4.

YSDP4 cells transformed with plasmids according to the present invention were grown on medium as follows: pap100S in YNB/glu/YE; pap100M in YNB/-glu/YE; pap100S in YNB/gal/YE/CAA; pap100M in SD/gal/0.1% YE/CAA; pCOM(Scepo)S [i.e. pCOM(-Scepo) single copy] in YNB/glu/YE/CAA; and pCOM(Scepo)M [i.e. pCOM(Scepo) multicopy] in YNB/glu/YE/CAA. The cells were incubated overnight with shaking at 30° C. Dilutions of 1:100 were prepared and cell number was determined for each culture before replating on YPD plates. The replated cultures were incubated at 30° C. for 3 days before replica plating onto the following media: YNB/CAA; YNB/glu/CAA/trp; YPD/400 μg/ml G418. These replica plates were incubated at 30° C. for 2 to 3 days. Colonies on the plates were counted and the percentages of cells containing the tryptophan marker and of cells exhibiting G418 resistance were determined as indicated in Table XIII wherein: "GLU" indicates culture in 2% glucose medium; "GAL" indicates culture in 2% galactose medium; and, "$G418^S$" indicates G418 sensitivity.

TABLE XIII

| No. | Type of Plasmid Medium | Total No. Clones | No. Trp+ | No. Trp− | No. $G418^R$ | No. $G418^S$ | % Trp+ | % $G418^R$ |
|---|---|---|---|---|---|---|---|---|
| 1 | PCOM(Scepo)S | 310 | 308 | 2 | 20 | 290 | 99.35 | 6.5 |
| 2 | PCOM(Scepo)M | 230 | 230 | 0 | 228 | 2 | 100.0 | 99.1 |
| 3 | pap100S GLU | 295 | 285 | 10 | 5 | 290 | 96.6 | 1.6 |
| 4 | pap100M GLU | 205 | 205 | 0 | 202 | 3 | 100.0 | 98.5 |
| 5 | pap100S GAL | 408 | 408 | 0 | 10 | 398 | 100.0 | 2.45 |
| 6 | pap100M GAL | 380 | 380 | 0 | 200 | 180 | 100.0 | 52.0 |

EXAMPLE 9

EPO expression

Cells from a fresh growth of pap100S on an SD plate and pap100M cells taken from a G418 plate were innoculated in YNB/CAA/glu/YE [i.e., YNB/CAA/glu containing 0.1% YE (yeast extract)] and incubated overnight with shaking at 30° C. On the next day, these cells were spun down, washed once with YNB/glu/-CAA and suspended in 10 ml of YNB/CAA/gal (i.e., YNB/CAA/ containing 2% galactose) before being transferred into YNB/CAA/YE/gal medium. The pap100S culture was stopped at 54 hours (O.D. 14.0) while the pap100M was stopped at 78 hours (O.D. 7.4). After each culture was stopped, the solutions were centrifuged. The supernatant was collected and a 1 ml sample was saved for radioimmunoassay. The rest of the supernatant was concentrated by ultra filtration. pCOM(Scepo) DNA samples were similarly prepared.

A radioimmunoassay for erythropoietin (EPO) was performed on the 1 ml sample. This assay employed labelled antibodies to EPO as disclosed in Egrie, U.S. patent application Ser. No. 463,724 (allowed) (incorporated by reference herein). As indicated in Table XIV, dilutions were prepared from each sample by the addition of phosphate buffered saline (PBS) containing 0.1% bovine serum albumin (BSA) and 0.025% sodium acetate.

TABLE XIV

| | | | SECRETED EPO | |
|---|---|---|---|---|
| No. | Sample | $A_{600}$ | Actual µg/ml | µg/OD Liter |
| 1 | pCOM(Scepo)S | 7.0 | 20.4 ± 4.7 | 41.7± |
| 2 | pCOM(Scepo)M | 5.3 | 2.25 ± 0.23 | 6.1± |
| 3 | pap100S GLU | 4.9 | <0.5 | <1.5 |
| 4 | pap100M GLU | 4.5 | ~1 | <3 |
| 5 | pap100S GAL | 5.9 | 82.75 ± 2.28 | 200.6 |
| 6 | pap100M GAL | 4.0 | 67.2 ± 4.4 | 240± |

As indicated by the results as shown in Table XIV, the expression of secreted EPO in pap100 was much higher than in pCOM(Scepo). There was a slightly higher production of EPO in the multicopy state of pap 100 as opposed to the single copy state. On the other hand, the multicopy state of the pCOM(Scepo) was much lower than the single copy state. This curious result may be due to fact that the multicopy state of pCOM(Scepo) induced an aberration in the expression of MFα promoter controlled expression. However, the regulated GPD hybrid-GAL promoter is superior to the MFα promoter system in this case. Furthermore, the expression of genes by this promoter is tightly regulated by galactose.

Northern blot analysis

The following types of cells were incubated overnight at 30° C. in 100 ml YNB/CAA/YE plus 2% glucose or 2% galactose as indicated: YSDP4 cells containing pap100S (+glucose); YSDP4 cells containing pap100M (+glucose); YSDP4 cells containing pap100S (+galactose); YSDP4 cells containing pap100M [+galactose); YSDP4 cells containing pCOM(Scepo)S (+glucose); YSDP4 cells containing pCOM(Scepo)M (+glucose); YSDP4 cells (+glucose); and YSDP4 cells (+galactose). Next, a sample of RNA was extracted from each type of cells and each sample was subjected to agarose gel electrophoresis. After blotting on nitrocellulose paper, the gel was placed on top of nitrocellulose paper and covered with saran wrap surrounded by a weighted glass plate. Blotting continued for 2 to 3 hours after which the filter was checked under unltraviolet light. Next the filter was baked at 80° C. for 2 hours and then washed briefly in hot boiling water.

The filter was incubated in a prehybridization mixture (0.1% SDS; 6 X SSC; 5 X Denhardt's solution [0.1% bovine serum albumin; 0.1% Ficoll; and 0.1% polyvinylpyrolidone] and, 100 µg/ml salmon sperm DNA) for 2 hours at 46° C.

A hybridization reaction was performed for 16 hours at 46° C. in the prehybridization solution, including an oligonucleotide probe (within a Seal-A-Meal bag TM available from Sears, Chicago, Ill.). The next day the bag was opened and the filter was washed. The kinased probe was prepared according to Zoller & Smith, supra and is complementary in sequence to the prepro region of MFα gene. Next the filter was washed, blot dried and autoradiographed.

The oligonucleotide probe had the sequence

3'TCTTACTCTAAAGGAAGTTAAAA 5'       (2)

The results of the Northern blot analysis of EPO mRNA are presented in Table XV.

TABLE XV

| | State | Load | Relative Amount mRNA | Ratio Multicopy: Single copy |
|---|---|---|---|---|
| pap100 in galactose | Single | 1 | 8300 | |
| | Single | 2 | 30435 | |
| | for average load | 1 | 11800 | |
| pap100 in galactose | Multicopy | 1 | 58650 | |
| | | 2 | 122781 | |
| | for average load | 1 | 60025 | 5.1 |

In Table XV, load 1 and load 2 respectively refer to 1 volume and 2 volumes of loads of equal quantitites (as determined by the absorbance at 260 nM) of RNA These results indicate that, in cells grown on galactose, there is 5 times as much EPO mRNA in pap100M cells than in pap100S cells.

While the present invention has been described in terms of preferred embodiments, it is expected that those skilled in the art will make further modifications and improvements upon the invention as disclosed. For example, the centromere sequence may be inserted downstream of any suitable promoter including, for example, gal2 or suc2. It is desirable to have recombinant plasmid copy number under the control of a CEN sequence during growth of a yeast culture to high cell density to avoid the accumulation of toxic gene products. On the other hand, at a high cell density, it would be desirable for copy number to be free of CEN control in order to permit copy number, and hence foreign gene expression levels, to increase dramatically to a high level. Such control followed by an increase might be provided by introducing a transcriptionally controlled CEN sequence according to the present invention along with the 2µ mechanism, for example. Moreover, although a G418 multicopy-selection concentration of greater than about 400 µg/ml has been exemplified in a specific strain herein, other strains may differ in sensitivity so that the multicopy selection concentration may be determined by a calibration run for each strain used. Therefore, it is intended that the scope of the present invention include all such modifications and variations which come within the scope of the invention as claimed.

What is claimed is:

1. A vector for the expression of a foreign gene in yeast comprising:
   a first regulatable promoter;
   a first terminator defining a region of transcription initiated at said first promoter;
   a centromere sequence located between said first promoter and said first terminator and under transcriptional control of said first promoter; and
   a replication sequence located outside said region of transcription.

2. The yeast vector as recited in claim 1, further comprising:
   a second promoter;
   a second terminator defining a region of termination for transcription initiated at said second promoter; and a gene foreign to the organism, said gene being located between said second promoter and said second terminator and being under the transcription control of the second promoter.

3. The yeast vector as recited in claim 2, further comprising:
means for selecting for cells containing the vector.

4. The yeast vector as recited in claim 1, further comprising:
means for selecting for cells containing the vector.

5. The yeast vector as recited in claim 1, further comprising:
a unique restriction site located outside said region of transcription.

6. The yeast vector as recited in claim 1 wherein the first promoter is a copper chelatin promoter.

7. The yeast vector as recited in claim 2 wherein the gene is a gene encoding an erythropoietic polypeptide.

8. A yeast vector for the expression of an erythropoietic foreign gene in yeast comprising:
a first regulatable promoter;
a first terminator defining a region of transcription initiated at said first promoter;
a centromere sequence located between said first promoter and said first terminator and under transcriptional control of said first promoter;
a replication sequence located outside said region of transcription;
a second promoter;
a second terminator defining a region of termination for transcription initiated at said second promoter; and
a gene encoding an erythropoietic polypeptide, said gene being located between said second promoter and said second terminator and being under the transcriptional control of the second promoter.

9. A method for providing for reversible control of vector copy number and for maintaining vector stability in yeast comprising the step of:
inserting into said vector a regulatable promoter, a terminator defining a region of transcription initiated at the promoter, a centromere sequence located between the promoter and the terminator and under transcriptional control of said first promoter, and a replication sequence located outside said region of transcription.

10. The method in yeast as recited in claim 9, further comprising the steps of:
transforming a cell with the vector; and
culturing the cell under conditions which do not activate transcription at the promoter.

11. The method in yeast as recited in claim 10 further comprising the step of:
altering the conditions of culture so that transcription is activated at the promoter.

12. A method for providing for reversible control of plasmid copy number, for providing cell lines having multiple copies of centromere-containing plasmids and for maintaining plasmid stability in yeast comprising the step of:
inserting into the plasmid a regulatable promoter, a terminator defining a region of transcription initiated at the promoter, a centromere sequence located between the promoter nd the terminator and under transcriptional control of said first promoter, and a replication sequence located outside said region of transcription.

13. The method in yeast as recited in claim 12, further comprising the steps of:
transforming a cell with the plasmid and
culturing the cell under conditions which do not activate transcription at the promoter.

14. The method in yeast as recited in claim 13 further comprising the step of:
altering the conditions of culture so that transcription is activated at the promoter.

15. A method for providing for reversible control of vector copy number and for maintaining vector stability in yeast comprising the step of:
inserting into a vector a copper chelatin promoter, a copper chelatin terminator defining a region of transcription initiated at the copper chelatin promoter, a centromere sequence located between the copper chelatin promoter and the copper chelatin terminator and under transcriptional control of said copper chelatin promoter, and a replication sequence located outside said region of transcription.

16. The method in yeast as recited in claim 15, further comprising the steps of:
transforming a cell with the vector; and
culturing the cell in a medium having a lower copper concentration than the concentration required to activate transcription at the copper chelatin promoter.

17. The method in yeast as recited in claim 16, further comprising the step of:
altering the conditions of culture so that the medium comprises at least the copper concentration required to activate transcription at the copper chelatin promoter.

18. A method in yeast for providing for reversible control of vector copy number and for maintaining vector stability in yeast comprising the steps of:
transforming a cell with a vector comprising: an antibiotic resistance gene; a first regulatable promoter, a first terminator defining a region of termination for transcription initiated at the promoter, a centromere sequence located between the first promoter and the first terminator and under transcriptional control of said first promoter, and a replication sequence located outside of said region of transcription; and a second promoter, a second terminator defining a region of transcription initiated at said second promoter, and an exogenous gene located between the second promoter and the second terminator, the second promoter;
maintaining the cell under conditions which do not activate transcription at the first promoter so that the cell may multiply to high cell density at low plasmid copy number;
altering the conditions of culture so that transcription is activated at the first promoter; and
applying selection pressure to the cells so that the copy number of plasmids containing the exogenous gene is increased leading to increased expression of the exogenous gene.

19. The method in yeast for providing reversible control of vector opy number and for maintaining vector stability as recited in claim 18 wherein said antibiotic resistance gene is a G418 gene, and said step of applying selection pressure comprises the step of culturing the cells in a medium comprising G418.

20. The method for providing reversible control of vector copy number and for maintaining vector stability in yeast as recited in claim 18:

wherein said inserting step comprises the step of introducing a copper chelatin promoter, a copper chelatin terminator, and a centromere sequence located between the copper chelatin promoter and the copper chelatin terminator and under transcriptional control of said copper chelatin promoter; and wherein said culturing step comprises the step of maintaining the cell in a medium having a lower copper concentration than the concentration required to activate transcription at the copper chelatin promoter; and wherein said step of altering the conditions of culture comprises the step of controlling medium copper concentration so that the medium has at least the copper concentration required to activate transcription at the copper chelatin promoter.

21. A strain of yeast cells comprising cells having on average more than two copies of a centromere-containing plasmid stably retained within the cells wherein said plasmid comprises the vector of claim 1.

* * * * *